(12) United States Patent
Jan et al.

(10) Patent No.: US 8,518,847 B2
(45) Date of Patent: Aug. 27, 2013

(54) AROMATIC ALKYLATION CATALYST

(75) Inventors: Deng-Yang Jan, Elk Grove Village, IL (US); James A. Johnson, Clarendon Hills, IL (US); Robert J. Schmidt, Barrington, IL (US); Mathias P. Koljack, Gilberts, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/879,363

(22) Filed: Sep. 10, 2010

(65) Prior Publication Data

US 2011/0077442 A1    Mar. 31, 2011

Related U.S. Application Data

(60) Provisional application No. 61/247,255, filed on Sep. 30, 2009.

(51) Int. Cl.
*B01J 29/06*    (2006.01)

(52) U.S. Cl.
USPC ............... 502/60; 502/63; 502/64; 502/85; 423/700

(58) Field of Classification Search
USPC ............... 502/60, 63, 64, 85; 423/700
See application file for complete search history.

(56) References Cited

U.S. PATENT DOCUMENTS

| | | |
|---|---|---|
| 3,204,005 A | 8/1965 | Nixon |
| 3,631,120 A | 12/1971 | Eberly, Jr. et al. |
| 3,641,177 A | 2/1972 | Eberly, Jr. et al. |
| 5,081,323 A | 1/1992 | Innes et al. |
| 6,111,157 A | 8/2000 | Hendriksen et al. |
| 6,756,030 B1 | 6/2004 | Rohde et al. |
| 6,909,026 B2 | 6/2005 | Dandekar et al. |
| 7,091,390 B2 | 8/2006 | Jan et al. |
| 7,268,267 B2 | 9/2007 | Jan et al. |
| 7,381,676 B1 | 6/2008 | Elia et al. |
| 7,683,228 B2 | 3/2010 | Brown |
| 7,812,196 B2 | 10/2010 | Dakka |
| 2003/0204121 A1 | 10/2003 | Miller |
| 2005/0197517 A1 | 9/2005 | Cheng et al. |
| 2008/0086018 A1 | 4/2008 | Cheng |

FOREIGN PATENT DOCUMENTS

| | | |
|---|---|---|
| EP | 0 014546 B1 | 2/1983 |
| EP | 0 306181 A2 | 3/1989 |

OTHER PUBLICATIONS

Wang, H., et al.; Surface Acidity of H-beta and Its Catalytic Activity for Alkylation of Benzene with Propylene; Catalysis Letters vol. 76, No. 3-4, 2001; pp. 225-229.

"Acid Strength Distribution and Catalytic Properties of H-ZSM-5: Effect of Deammoniation Conditions of NH4-ZSM-5," Vikram S. Nayak et al., Journal of Catalysis 81, 26-45 (1983).

"Solid State NMR Spectroscopy Applied to Zeolites," G. Engelhardt, Studies in Surface and Catalysis 137, Elsevier Science B.V., 387-418 (2001).

*Primary Examiner* — Elizabeth Wood
(74) *Attorney, Agent, or Firm* — Mark R Willis

(57) ABSTRACT

A aromatic alkylation catalyst, processes for producing the catalyst, and aromatic alkylation processes employing the catalysts are disclosed. The catalyst comprises a UZM-8 zeolite and nitrogen, and the catalyst has a nitrogen to zeolite aluminum molar ratio of at least about 0.015. In an exemplary alkylation process, the catalyst provides improved product yield.

14 Claims, No Drawings

AROMATIC ALKYLATION CATALYST

CROSS-REFERENCE TO RELATED APPLICATION

This application claims the benefit of U.S. Provisional Application No. 61/247,255 filed Sep. 30, 2009.

FIELD OF THE INVENTION

This invention relates to the alkylation of aromatic compounds. More specifically, the invention relates to catalysts used to produce monoalkylated aromatics; and methods of making and using the catalysts. The catalysts find use, for example, in the production of cumene and ethylbenzene.

BACKGROUND OF THE INVENTION

Alkylation of aromatic compounds with a C2 to C4 olefin and transalkylation of polyalkylaromatic compounds are two common reactions for producing monoalkylated aromatic compounds such as cumene and ethylbenzene. Examples of these two reactions that are practiced industrially to produce cumene (isopropylbenzene) are the alkylation of benzene with propylene and the transalkylation of benzene and a diisopropylbenzene (DIPB). The alkylation reaction forms cumene and common byproducts such as DIPBs and triisopropylbenzenes (TIPBs). DIPBs, TIPBs, and some of the higher polyisopropylbenzenes can be readily transalkylated by benzene to produce cumene. Alkylation and transalkylation reactions may be combined in one process unit in a single reaction zone or multiple reaction zones.

Many aromatic alkylation catalysts containing a variety of zeolites have been proposed and used for alkylating and transalkylating aromatics. Regardless whether the reaction is alkylation or transalkylation, it is important that such catalysts exhibit acceptable activity to convert the reactants and acceptable yield to the desired product. Although compounds containing nitrogen may be used in the synthesis and/or treatment of such zeolites, nitrogen is known to reduce the activity of the resulting catalysts. Therefore it is well known in the art to remove nitrogen such as by heating for sufficient time and temperature to obtain the hydrogen form of the zeolite. It is also known that nitrogen compounds in the reactants may be adsorbed on the active catalyst sites and cause rapid deactivation of the catalyst. The effect of nitrogen on the selectivity of such catalysts is inconsistent as both increased and decreased selectivity has been reported. The source or sources of the inconsistent selectivity changes is uncertain as differences in one or more variables, such as, types of zeolites, zeolite treatments steps, catalyst compositions and preparation steps, the reactants, desired products, and various reaction conditions have been reported.

Catalysts having superior yield are desirable because they may be used to reduce the construction and/or operating costs of a process unit since recycle and waste streams are reduced. At the same time, the catalyst activity and stability must be maintained at levels sufficient to avoid eliminating the benefit conferred by the increased yield. It is desired that the activity and stability be sufficient to enable use of the catalyst in existing processing units.

SUMMARY OF THE INVENTION

The invention relates to an aromatic alkylation catalyst comprising UZM-8 zeolite, and nitrogen. In an exemplary alkylation process, the catalyst provides improved product yield while exhibiting little or no loss of activity.

In an embodiment, the invention is an aromatic alkylation catalyst comprising a UZM-8 zeolite and nitrogen, the catalyst having a nitrogen to zeolite aluminum molar ratio of at least about 0.015.

In another embodiment, the invention is a process for producing an aromatic alkylation catalyst comprising: forming a UZM-8 zeolite to produce a formed catalyst; heating the formed catalyst at conditions including a temperature of from about 300° C. to about 650° C. for a period of from about 10 minutes to about 20 hours to produce a calcined catalyst; ion exchanging the calcined catalyst with an ion exchange solution comprising ammonium ions at ion exchange conditions to produce an ion exchanged catalyst; and heating the ion exchanged catalyst at conditions including a temperature of from about 300° C. to about 650° C. for a period of from about 10 minutes to about 20 hours to produce the aromatic alkylation catalyst comprising the UZM-8 zeolite and nitrogen, the catalyst having a nitrogen to zeolite aluminum molar ratio of at least about 0.015.

In a further embodiment, the invention is an aromatic alkylation process comprising contacting an alkylatable aromatic compound and an olefin with an aromatic alkylation catalyst at aromatic alkylation conditions to produce an alkylated aromatic compound, the aromatic alkylation catalyst comprising a UZM-8 zeolite and nitrogen, the catalyst having a nitrogen to zeolite aluminum molar ratio of at least about 0.015.

DETAILED DESCRIPTION OF THE INVENTION

Catalysts of the invention comprise one or more members of the family of zeolites designated UZM-8. As used herein, UZM-8 includes the aluminosilicate and substituted aluminosilicate zeolites described in U.S. Pat. No. 6,756,030 and the modified UZM-8 zeolites, such as, UZM-8HS which are described in U.S. Pat. No. 7,091,390. U.S. Pat. Nos. 6,756,030 and 7,091,390, each of which is herein incorporated by reference in its entirety, provide detailed descriptions of the UZM-8 zeolites and methods for the preparation thereof. Therefore it is not necessary herein to describe these in detail. Briefly, UZM-8 zeolites may be prepared in an alkali-free reaction medium in which only one or more organoammonium species are used as structure directing agents. In this case, the microporous crystalline UZM-8 zeolite has a composition in the as-synthesized form and on an anhydrous basis expressed by the empirical formula:

$$R_r^{p+}Al_{(1-x)}E_xSi_yO_z$$

where R is at least one organoammonium cation selected from the group consisting of protonated amines, protonated diamines, quaternary ammonium ions, diquaternary ammonium ions, protonated alkanolamines and quaternized alkanolammonium ions. Preferred organoammonium cations are those that are non-cyclic or those that do not contain a cyclic group as one substituent. Of these, those that contain at least two methyl groups as substituents are especially preferred. Examples of preferred cations include without limitation DEDMA, ETMA, HM and mixtures thereof. The ratio of R to (Al+E) is represented by "r" which varies from about 0.05 to about 5. The value of "p" which is the weighted average valence of R varies from 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron.

The mole fraction of E is represented by "x" and has a value from 0 to about 0.5, while "z" is the mole ratio of O to (Al+E) and is given by the equation $$z = (r \cdot p + 3 + 4 \cdot y)/2$$

The UZM-8 zeolites can be prepared using both organoammonium cations and alkali and/or alkaline earth cations as structure directing agents. As in the alkali-free case above, the same organoammonium cations can be used here. Alkali or alkaline earth cations are observed to speed up the crystallization of UZM-8, often when present in amounts less than 0.05 M⁺/Si. For the alkali and/or alkaline earth metal containing systems, the UZM-8 zeolite has a composition in the as-synthesized form and on an anhydrous basis expressed by the empirical formula:

$$M_m^{n+} R_r^{p+} Al_{(1-x)} E_x Si_y O_z$$

where M is at least one exchangeable cation and is selected from the group consisting of alkali and alkaline earth metals. Specific examples of the M cations include but are not limited to lithium, sodium, potassium, rubidium, cesium, calcium, strontium, barium and mixtures thereof. Preferred R cations include without limitation DEDMA, ETMA, HM and mixtures thereof. The value of "m" which is the ratio of M to (Al+E) varies from about 0.01 to about 2. The value of "n" which is the weighted average valence of M varies from about 1 to about 2. The ratio of R to (Al+E) is represented by "r" which varies from 0.05 to about 5. The value of "p" which is the weighted average valence of R varies from about 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of O to (Al+E) and is given by the equation $$z = (m \cdot n + r \cdot p + 3 + 4 \cdot y)/2$$

where M is only one metal, then the weighted average valence is the valence of that one metal, i.e. +1 or +2. However, when more than one M metal is present, the total amount of $$M_m^{n+} = M_{m1}^{(n1)+} + M_{m2}^{(n2)+} + M_{m3}^{(n3)+} + \ldots$$

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

Similarly when only one R organic cation is present, the weighted average valence is the valence of the single R cation, i.e., +1 or +2. When more than one R cation is present, the total amount of R is given by the equation.

$$R_r^{p+} = R_{r1}^{(p1)+} + R_{r2}^{(p2)+} + R_{r3}^{(p3)+}$$

and the weighted average valence "p" is given by the equation $$p = \frac{p_1 \cdot r_1 + p_2 \cdot r_2 + p_3 \cdot r_3 + \ldots}{r_1 + r_2 + r_3 + \ldots}$$

The UZM-8 zeolites used in catalysts of the invention may be synthesized by a hydrothermal crystallization of a reaction mixture prepared by combining reactive sources of R, aluminum, silicon and optionally M and E. The sources of aluminum include but are not limited to aluminum alkoxides, precipitated aluminas, aluminum metal, sodium aluminate, organoammonium aluminates, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica, alkali silicates and organoammonium silicates. A special reagent consisting of an organoammonium aluminosilicate solution can also serve as the simultaneous source of Al, Si, and R. Sources of the E elements include but are not limited to alkali borates, boric acid, precipitated gallium oxyhydroxide, gallium sulfate, ferric sulfate, ferric chloride, chromium nitrate and indium chloride. Sources of the M metals include the halide salts, nitrate salts, acetate salts, and hydroxides of the respective alkali or alkaline earth metals. R can be introduced as an organoammonium cation or an amine. When R is a quaternary ammonium cation or a quaternized alkanolammonium cation, the sources include but are not limited the hydroxide, chloride, bromide, iodide and fluoride compounds. Specific examples include without limitation diethyldimethylammonium (DEDMA) hydroxide, ethyltrimethylammonium (ETMA) hydroxide, tetramethylammonium hydroxide, tetraethylammonium hydroxide, hexamethonium bromide, tetrapropylammonium hydroxide, methyltriethylammonium hydroxide, DEDMA chloride, tetramethylammonium chloride and choline chloride. R may also be introduced as an amine, diamine, or alkanolamine that subsequently hydrolyzes to form an organoammonium cation. Specific non-limiting examples are N,N,N',N'-tetramethyl-1,6-hexanediamine, triethylamine, and triethanolamine. Preferred sources of R without limitation are ETMAOH, DEDMAOH, and hexamethonium dihydroxide (HM(OH)₂).

The reaction mixture containing reactive sources of the desired components can be described in terms of molar ratios of the oxides by the formula:

$$aM_{2/n}O:bR_{2/p}O:1-cAl_2O_3:cE_2O_3:dSiO_2:eH_2O$$

where "a" varies from 0 to about 25, "b" varies from about 1.5 to about 80, "c" varies from 0 to 1.0, "d" varies from about 10 to about 100, and "e" varies from about 100 to about 15000. If alkoxides are used, it is preferred to include a distillation or evaporative step to remove the alcohol hydrolysis products. The reaction mixture is now reacted at a temperature of about 85° C. to about 225° C. (185 to 437° F.) and preferably from about 125° C. to about 150° C. (257 to 302° F.) for a period of about 1 day to about 28 days and preferably for a time of about 4 days to about 14 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C.

The UZM-8 aluminosilicate zeolite, which is obtained from the above-described process, is characterized by an x-ray diffraction pattern, having at least the d-spacings and relative intensities set forth in Table A below:

TABLE A d-Spacings and Relative Intensities for as-synthesized UZM-8

| 2-θ | d(Å) | I/I$_0$ % |
|---|---|---|
| 6.40-6.90 | 13.80-12.80 | w - s |
| 6.95-7.42 | 12.70-11.90 | m - s |
| 8.33-9.11 | 10.60-9.70 | w - vs |
| 19.62-20.49 | 4.52-4.33 | m - vs |
| 21.93-22.84 | 4.05-3.89 | m - vs |
| 24.71-25.35 | 3.60-3.51 | w - m |
| 25.73-26.35 | 3.46-3.38 | m - vs |

The UZM-8 compositions are stable to at least 600° C. (1112° F.) (and usually at least 700° C. (1292° F.)). The characteristic diffraction lines associated with typical calcined UZM-8 samples are shown below in table B. The as-synthesized form of UZM-8 is expandable with organic cations, indicating a layered structure.

TABLE B d-Spacings and Relative Intensity for Calcined UZM-8

| 2-θ | d(Å) | I/I$_0$ % |
|---|---|---|
| 4.05-4.60 | 21.80-19.19 | w - m |
| 7.00-7.55 | 12.62-11.70 | m - vs |
| 8.55-9.15 | 10.33-9.66 | w - vs |
| 12.55-13.15 | 7.05-6.73 | w |
| 14.30-14.90 | 6.19-5.94 | m - vs |
| 19.55-20.35 | 4.54-4.36 | w - m |
| 22.35-23.10 | 3.97-3.85 | m - vs |
| 24.95-25.85 | 3.57-3.44 | w - m |
| 25.95-26.75 | 3.43-3.33 | m - s |

In addition to as synthesized and calcined UZM-8 forms, the invention encompasses use of other UZM-8 forms including ion exchanged UZM-8 and modified UZM-8, for example, by dealumination as taught in U.S. Pat. No. 7,091,390.

Catalysts according to the invention comprise UZM-8 zeolite and nitrogen and may be prepared by processes comprising a forming step, a first calcining step, an ion exchange step and a final calcining step. One or more of these steps may be repeated, optional process steps may be used, and the order of the steps may be varied to produce catalysts according to the invention.

In the forming step, UZM-8 zeolite may be formed into various shapes such as pills, pellets, extrudates, spheres, granules, etc. as is known in the art to produce a formed catalyst. In an embodiment, UZM-8 zeolite is shaped into the formed catalyst without use of a binder. That is, although forming agents such as extrusion or pelletizing aides may be added to the zeolite, use of such additives that do not survive the heating or calcining steps result in a catalyst that is essentially UZM-8 zeolite. In another embodiment, UZM-8 zeolite is mixed with a binder prior to or during the forming step. For example, extrudates may be prepared by conventional means which involve mixing of zeolite with a suitable wetting agent to form a homogeneous dough or thick paste having the correct moisture content to produced formed catalyst extrudates with acceptable integrity to withstand direct calcination. Extrudates may also be formed by mixing the zeolite and a binder with a suitable peptizing agent to form the homogeneous dough or thick paste. The dough is extruded through a die to give the shaped extrudate. A multitude of different extrudate shapes are possible, including, but not limited to, cylinders, cloverleaf, dumbbell and symmetrical and asymmetrical polylobates. It is also within the scope of the invention that the extrudates may be further shaped to any desired form, such as spheres, by any means known in the art.

Spheres may be prepared by the well known oil-drop method which is described in U.S. Pat. No. 2,620,314 and is herein incorporated by reference in its entirety. The method involves dropping a mixture of zeolite, and for example, alumina sol, and gelling agent into an oil bath maintained at elevated temperatures. The droplets of the mixture remain in the oil bath until they set and form hydrogel spheres. The spheres are then withdrawn from the oil bath and typically subjected to aging treatments in oil and an ammoniacal solution to further improve their physical characteristics. The formed catalyst spheres are then washed and dried at a temperature of from about 50° C. to about 200° C. and subjected to a calcination procedure at a temperature of about 300° C. to about 650° C. for a period of about 0.5 to about 20 hours. This treatment effects conversion of the hydrogel to the corresponding alumina matrix. The invention is not limited by the specific forming technique and other methods for forming zeolites with and without a binder such as forming particles via accretion and forming pills or pellets via compression may be used.

One or more forms of UZM-8 may be used in preparing catalysts according to the invention and the invention contemplates the addition of optional zeolites, such as beta zeolite. The binder, when present, should preferably be porous, have a surface area of about 5 to about 800 m$^2$/g, and be relatively refractory to the conditions of the aromatic alkylation process. Non-limiting examples of binders include aluminas, titania, zirconia, zinc oxide, magnesia, boria, silica-alumina, silica-magnesia, chromia-alumina, alumina-boria, silica-zirconia, silica, silica gel, and clays. The binder may be amorphous silica and/or alumina, including gamma-, eta-, and theta-alumina, with gamma- and eta-alumina being preferred. In an embodiment, the binder contains less alkali and alkaline earth metals than the UZM-8 zeolite on a mass percent and volatile free basis. The binder may be devoid of alkali and alkaline earth metals.

In an embodiment, the UZM-8 zeolite and binder are mixed in proportion to obtain a aromatic alkylation catalyst having from about 5 mass % to about 99 mass % UZM-8 zeolite on a volatile free basis. In another embodiment, the aromatic alkylation catalyst comprises from about 10 mass % to about 90 mass % UZM-8 zeolite on a volatile free basis; and the aromatic alkylation catalyst may comprise from about 30 mass % to about 80 mass % UZM-8 zeolite on a volatile free basis. As used herein, the term "volatile free basis" means that the mass percent or concentrations of components are calculated based on the weight of the catalyst after volatiles, including water, have been removed by heating the catalyst at 900° C. for 4 hours.

In a first calcining step, the formed catalyst may be heated at conditions including a temperature of from about 300° C. to about 650° C. for a period of from about 10 minutes to about 20 hours to produce a calcined catalyst. In an embodiment, the first calcining conditions include a temperature of from about 400° C. to about 650° C. for a period of from about 10 minutes to about 10 hours; and the period may be from about 10 minutes to about 5 hours. In an embodiment, the first calcining step is conducted at a pressure from about 69 kPa(a) to about 138 kPa(a) (10 to 20 psia). The first calcining step atmosphere may be inert, such as nitrogen. In another embodiment the first calcining step atmosphere may comprise oxygen, for example, from about 1 to about 21 mole % oxygen; the atmosphere may be air. Other constituents such as water vapor and/or ammonia may also be present in the first calcining step atmosphere. The first calcining step may be conducted in a variety of batch and/or continuous equipment as is known in the art such as box ovens, belt ovens, and rotating kilns.

Prior to the first calcining step, an optional drying step may be conducted to dry the formed catalyst at a temperature of from about 100° C. to about 320° C. Typically, the drying time at temperature may range from about 1 to about 24 or more hours. The optional drying step may be conducted in air or in an inert atmosphere such as nitrogen. In addition to or in place of the optional drying step, an optional inert calcining step may be conducted prior to the first calcining step. The optional inert calcining step may be conducted in an inert atmosphere such as nitrogen at conditions including a temperature of from about 300° C. to about 650° C. for a period of from about 10 minutes to about 10 hours.

In an ion exchange step the calcined catalyst is contacted with a solution of ammonium ions at exchange conditions including a temperature of about 15° C. to about 100° C. and a time of about 20 minutes to about 50 hours to produce an ion exchanged catalyst. In an embodiment, the ion exchange conditions including a temperature of about 50° C. to about 90° C. and a time of about 1 hour to about 6 hours. The ion exchange solution may for example be a solution of from about 1 to about 20 mass % ammonium nitrate; and in an embodiment the ion exchange solution ranges from about 5 to about 15 mass % ammonium nitrate. Other non limiting example sources of ammonium ions include ammonium chloride and ammonium sulfate. In an embodiment, the ion exchanged catalyst has lower concentration of alkali and alkaline earth metals relative to the calcined catalyst.

The ion exchange step may be followed by an optional water wash step and multiple ion exchange steps may be used to obtain the desired amount of alkali and alkaline earth metals on the aromatic alkylation catalyst. In an embodiment, the aromatic alkylation catalyst contains less than 0.1 mass %, preferably less than 0.05 mass %, and more preferably less than 0.02 mass % of alkali and alkaline earth metals on a metal oxide, e.g. $Na_2O$, volatile free basis. Water washing after ion exchange is well known. Suitable conditions for the optional water washing step include a water to catalyst weight ratio ranging from about 1:1 to about 10:1 and a temperature ranging from about 15° C. to about 100° C. The water/catalyst contacting time will vary as is known in the art with the equipment and the type of contacting, e.g. flow through fixed bed, counter-current flows, and contact and decant. The ion exchanged catalyst may optionally be dried prior to the final calcining step. Suitable drying conditions include a temperature of from about 100° C. to about 320° C. for a period of from about 1 to about 24 or more hours. This optional drying step may be conducted in air or in an inert atmosphere such as nitrogen.

The ion exchanged catalyst is heated in a final calcining step wherein the nitrogen content of the catalyst may be controlled to produce the aromatic alkylation catalyst having a nitrogen to zeolite aluminum molar ratio (N/Alz) of at least about 0.015. In an embodiment, the nitrogen to zeolite aluminum molar ratio of the catalyst ranges from about 0.015 to about 0.5; the nitrogen to zeolite aluminum molar ratio may range from about 0.015 to about 0.43; and the nitrogen to zeolite aluminum molar ratio may range from about 0.015 to about 0.36. In another embodiment, the aromatic alkylation catalyst has a nitrogen to zeolite aluminum molar ratio ranging from about 0.045 to about 0.5; the nitrogen to zeolite aluminum molar ratio may range from about 0.045 to about 0.43; the nitrogen to zeolite aluminum molar ratio may range from about 0.045 to about 0.36; and the nitrogen to zeolite aluminum molar ratio may range from about 0.045 to about 0.3. In a further embodiment, the aromatic alkylation catalyst has a nitrogen to zeolite aluminum molar ratio ranging from 0.09 to about 0.5; the nitrogen to zeolite aluminum molar ratio may range from about 0.09 to about 0.43; the nitrogen to zeolite aluminum molar ratio may range from about 0.09 to about 0.36; the nitrogen to zeolite aluminum molar ratio may range from about 0.09 to about 0.3; and the nitrogen to zeolite aluminum molar ratio may range from about 0.09 to about 0.27. The nitrogen to zeolite aluminum molar ratio, is calculated from the mass of nitrogen on the aromatic alkylation catalyst as determined by method ASTM 5291 and the total mass (framework and non framework) of aluminum in the UZM-8 zeolite in the catalyst. Thus, the zeolite aluminum mass is determined by the aluminum content of the zeolite as measured by inductively coupled plasma—atomic emission spectroscopy (ICP-AES) and the zeolite weight percentage in the catalyst. Unless otherwise noted, the analytical methods used herein such as ASTM 5291 are available from ASTM International, 100 Barr Harbor Drive, West Conshohocken, Pa., USA.

In the final calcining step, the ion exchanged catalyst may be heated at conditions including a temperature of from about 300° C. to about 650° C. for a period of from about 10 minutes to about 20 hours to produce the aromatic alkylation catalyst. In an embodiment, the final calcining conditions include a temperature of from about 400° C. to about 650° C. for a period of from about 10 minutes to about 10 hours; and the period may be from about 10 minutes to about 5 hours. In an embodiment, the final calcining step is conducted at a pressure from about 69 kPa(a) to about 138 kPa(a) (10 to 20 psia). The final calcining step atmosphere may be inert, such as nitrogen. In another embodiment the final calcining step atmosphere may comprise oxygen, for example, from about 1 to about 21 mole % oxygen; the atmosphere may be air. Other constituents such as water vapor and/or ammonia may also be present in the final calcining step atmosphere. The final calcining step may be conducted in a variety of batch and/or continuous equipment as is known in the art such as box ovens, belt ovens, and rotating kilns The conditions of the final calcining step may be the same as or different from the conditions of the first calcining step.

The final calcining conditions are adjusted as needed to obtain the level of nitrogen on the aromatic alkylation catalyst that will result in the desired nitrogen to zeolite aluminum molar ratio. The precise final calcining conditions may vary with number, type, and conditions of the prior processing steps employed and with the specific equipment and conditions, such as the atmosphere and heating and cooling rates, used to perform the final calcining step. In general, adjustments to the final calcining step temperature and time at temperature provide the greatest change in the nitrogen content and N/Alz of the aromatic alkylation catalyst produced. For example, with other variables held constant, the nitrogen content of the catalyst will increase as the calcination time and/or temperature are decreased. Generally, calcination conditions that are less severe, i.e. causing less zeolite dealumination will result in catalysts with higher nitrogen contents.

The alkylation of aromatic compounds involves reacting an alkylatable aromatic compound with an olefin using the above described zeolitic catalyst to produce an alkylated aromatic and in an embodiment a monoalkylated aromatic. The olefins which can be used in the instant process are any of those which contain from 2 up to about 20 carbon atoms, that is C2 to C20 olefins. These olefins may be branched or linear olefins and either terminal or internal olefins. Preferred olefins are ethylene, propylene and those olefins which are known as detergent range olefins. Detergent range olefins are linear olefins containing from 6 up through about 20 carbon atoms which have either internal or terminal double bonds used to produce detergent range linear alkylbenzene. Linear olefins containing from 8 to 16 carbon atoms are preferred and those containing from 10 up to about 14 carbon atoms are especially preferred. More than one feed olefin may be used. Sources of olefinic feed streams containing mixtures of olefins include refinery FCC propane/propylene streams, naphtha cracking unit off gases, gas plant off gases, and other refinery streams.

The alkylatable aromatic compounds may be selected from the group consisting of benzene, naphthalene, anthracene, phenanthrene, and substituted derivatives thereof, with benzene and its derivatives being the most preferred aromatic compound. By alkylatable is meant that the aromatic compound can be alkylated by an olefinic compound. The alkylatable aromatic compounds may have one or more of the substituents selected from the group consisting of alkyl groups having from 1 to about 20 carbon atoms, hydroxyl groups, and alkoxy groups whose alkyl group also contains from 1 up to 20 carbon atoms. Where the substituent is an alkyl or alkoxy group, a phenyl group can also can be substituted on the alkyl chain. Although unsubstituted and mono-substituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, etc.; phenol, cresol, anisole, ethoxy-, propoxy-, butoxy-, pentoxy-, hexoxybenzene, etc. More than one feed aromatic can be used. Sources of benzene, toluene, xylene, and or other feed aromatics include product streams from naphtha reforming units, aromatic extraction units, and petrochemical complexes for the producing para-xylene and other aromatics.

The basic configuration of a catalytic aromatic alkylation process is known in the art. The feed aromatic and the feed olefin are preheated and charged to an alkylation zone containing generally from one to four reactors in series. Suitable cooling means may be provided between reactors to compensate for the net exothermic heat of reaction in each of the reactors. Suitable means may be provided upstream of or with each reactor to charge additional feed aromatic, feed olefin, or other streams (e.g., effluent of a reactor, or a stream containing one or more polyalkylbenzenes) to any reactor in the alkylation zone. Each alkylation reactor may contain one or more alkylation catalyst beds. The invention encompasses dual zone aromatic alkylation processes such as those as described in U.S. Pat. No. 7,420,098 which is herein incorporated by reference in its entirety.

The particular conditions under which the alkylation reaction is conducted depends upon the aromatic compound and the olefin used. One necessary condition is that the reaction be conducted under at least partial liquid phase conditions. Therefore, the reaction pressure is adjusted to maintain the olefin at least partially dissolved in the liquid phase. For higher olefins the reaction may be conducted at autogenous pressure. The alkylation conditions usually include a pressure in the range between about 1379 kPa(g) and 6985 kPa(g) (200-1,000 psig). In an embodiment, the pressure ranges between about 2069 kPa(g) and 4137 kPa(g) (300-600 psig). The alkylation of the alkylatable aromatic compounds with the olefins in the C2-C20 range can be carried out at a temperature of about 60° C. to about 400° C., and preferably from about 90° C. to about 250° C., for a time sufficient to form the desired product. In a continuous process this time can vary considerably, but is usually from about 0.1 to about 8 $hr^{-1}$ weight hourly space velocity (WHSV) with respect to the olefin. As used herein, weight hourly space velocity of a component means the weight flow rate of the component per hour divided by the catalyst weight in the same units of measure. In particular, the alkylation of benzene with ethylene can be carried out at temperatures of about 200° C. to about 250° C. and the alkylation of benzene with propylene at a temperature of about 90° C. to about 200° C. The ratio of alkylatable aromatic compound to olefin used in the instant process will depend upon the degree of monoalkylation desired as well as the relative costs of the aromatic and olefinic components of the reaction mixture. For alkylation of benzene by propylene, the benzene-to-olefin molar ratio may be as low as about 0.1 and as high as about 10, with a ratio of about 0.5 to about 3 being preferred. Where benzene is alkylated with ethylene a benzene-to-olefin ratio may be between about 0.1 and 10, with a ratio of about 0.5 to about 4 being preferred. For detergent range olefins of C6-C20, a benzene-to-olefin ratio of between about 5 and about 30 is generally sufficient to obtain the desired monoalkylation yield, with a range between about 8 and about 20 even more preferred.

The following examples illustrate embodiments of the instant invention.

EXAMPLE 1

In a large beaker 160.16 grams of diethyldimethylammonium hydroxide was added to 1006.69 grams de-ionized water, followed by 2.79 grams of 50 wt % NaOH solution. Next, 51.48 grams of liquid sodium aluminate was added slowly and stirred for 20 minutes. Then, 178.89 grams of Ultrasil ($SiO_2$) was slowly added to the gel and stirred for 20 minutes. Next, 24 grams of UZM-8 seed was added to the gel and stirred for an additional 20 minutes. The gel was then transferred to a 2-liter stirred reactor and heated to 160° C. in 2 hours, and crystallized for 115 hours. After digestion, the material was filtered and washed with de-ionized water and dried at 100° C. XRD (X-Ray Diffraction) analysis showed a pure UZM-8 material. The elemental analysis by inductively coupled plasma—atomic emission spectroscopy (ICP-AES) was Si=41.4 wt %, Al=3.9 wt %, Na=1.93 wt % corresponding to $Si/Al_2$=20.47, and C=7.6%, H=2.21% and N=1.45 wt %. A portion of the zeolite was calcined at 550° C., ammonium exchanged and then calcined at 550° C. to obtain a BET surface area of 462 $m^2$/g, a total pore volume of 1.607 cc/g, and a micropore volume of 0.105 cc/g by $N_2$ adsorption isotherm. Surface area and pore volume are calculated using nitrogen partial pressure $p/p_o$ data points ranging from about 0.03 to about 0.30 using the BET (Brunauer-Emmett-Teller) model method using nitrogen adsorption technique as described in ASTM D4365-95, Standard Test Method for Determining Micropore Volume and Zeolite Area of a Catalyst, and in the article by S. Brunauer et al., J. Am. Chem. Soc., 60(2), 309-319 (1938).

The UZM-8 zeolite was dried at 100° C. for 12 hours and extruded into pellets of cylindrical extrudate of 1/16" diameter containing 70 mass % zeolite and 30 mass % alumina on a volatile free basis. The formed catalyst was dried at 110° C. for 2 hours, and calcined in a rotary kiln at about 600° C. for about 1 hour in flowing air. The calcined extrudate was ammonium exchanged using a ammonium nitrate solution of about 10 wt % at about 65° C. for 2 hours to lower the sodium content below 1000 wppm as Na₂O on a volatile free basis and dried at about 100° C. for 2 hours to produce a dried, ion exchanged extrudate.

EXAMPLE 2 (Comparative)

A portion of the dried, ion exchanged extrudate from Example 1 was passed through a rotary kiln wherein the extrudate was heated in flowing air at about 620° C. for about 1 hour to produce Catalyst A. The nitrogen to zeolite aluminum molar ratio (N/Alz) for each of the catalysts prepared was determined as described above and is reported below in Table 1.

EXAMPLE 3

A second portion of the dried, ion exchanged extrudate from Example 1 was heated in a box oven in flowing air at 3° C. per minute to a 425° C. hold temperature and was held at the hold temperature for 1 hour. The catalyst was then cooled down to 110° C. to produce Catalyst B.

EXAMPLE 4

A third portion of the dried, ion exchanged extrudate from Example 1 was heated in a box oven in flowing air at 3° C. per minute to a 450° C. hold temperature and was held at the hold temperature for 1 hour. The catalyst was then cooled down to 110° C. to produce Catalyst C.

EXAMPLE 5

A fourth portion of the dried, ion exchanged extrudate from Example 1 was heated in a box oven in flowing air at 10° C. per minute to a 550° C. hold temperature and was held at the hold temperature for 10 minutes. The catalyst was removed from the oven at temperature to produce Catalyst D.

EXAMPLE 6

A second batch of dried, ion exchanged extrudate was prepared using the same zeolite synthesis and drying, catalyst forming, calcination, ammonium ion exchange and drying steps described in Example 1.

EXAMPLE 7

A portion of the dried, ion exchanged extrudate from Example 6 was passed through a rotary kiln wherein the catalyst was heated in flowing air at about 566° C. for about 1 hour to produce Catalyst E.

EXAMPLE 8

A second portion of the dried, ion exchanged extrudate from Example 6 was passed through a rotary kiln wherein the catalyst was heated in flowing air at about 593° C. for 1 hour to produce Catalyst F.

EXAMPLE 9

A third batch of dried, ion exchanged extrudate was prepared using the same zeolite synthesis and drying, catalyst forming, calcination, ammonium ion exchange and drying steps described in Example 1.

EXAMPLE 10

A portion of the dried, ion exchanged extrudate from Example 9 was passed through a rotary kiln wherein the catalyst was heated in flowing air at about 500° C. for about 1 hour to produce Catalyst G.

EXAMPLE 11

Each of Catalysts A through G described above were evaluated according to the following procedure. 50 cc of a catalyst was loaded into a 22 mm internal diameter reactor equipped with thermal-well in a 3-zone furnace. The catalyst was dried in benzene at 250° C. at 3447 kPa(g) plant pressure. After the catalyst dry-down, the temperature was lowered to achieve a reactor inlet temperature of 120° C. Thereafter, a portion of the effluent benzene was recycled and propylene was introduced to achieve an olefin WHSV of around 1.1 hr$^{-1}$, a benzene to propylene molar ratio of 2.0 and an effluent to fresh feed weight ratio of 6.0. The product effluent was sampled and analyzed using on-line GC. The desired product yield, e.g. cumene, is reported as the mole ratio of cumene produced divided by the sum of the cumene and DIPB produced and is reported as a percentage. The temperature profiles along the catalyst bed were monitored to determine the catalyst activity. The activity of the catalyst is defined as the end of active zone (EAZ), that is where olefin, e.g. propylene, consumption is complete, and is reported as a percentage of the length of the catalyst bed.

The end of active zone, is derived by plotting the temperature profiles, i.e. the temperature relative to the position along the catalysts bed and is defined by the intersection of a line drawing through the linear portion of the temperature rise and a horizontal line defined by the maximum temperature and reported as a percentage of the catalyst bed. More active catalysts correspond to lower EAZ as a smaller fraction of catalyst bed is required to achieve complete olefin conversion. The test results are summarized below in table 1.

TABLE 1

| Catalyst | Final Calcination Temp, ° C. | N/Alz, molar ratio | Yield, Cumene/ (Cumener + DIPB) molar ratio as % | Activity, EAZ as % of catalyst bed |
|---|---|---|---|---|
| A | 620 | 0.009 | 82.5 | 23 |
| B | 425 | 0.120 | 84.5 | 31 |
| C | 450 | 0.047 | 83.3 | 18 |
| D | 550 | 0.127 | 83.8 | 34 |
| E | 566 | 0.133 | 83.8 | 38 |
| F | 593 | 0.093 | 83.2 | 28 |
| G | 500 | 0.234 | 85.3 | 58 |

As shown in Table 1, the yield of cumene increases with the nitrogen to zeolite aluminum molar ratio (N/Alz) of the catalyst, while the adverse impact on activity is minimal. For example, based on the above data it is estimated that a nitrogen to zeolite aluminum molar ratio (N/Alz) of about 0.5 for the conditions tested would fully utilize the catalyst bed to convert the olefins, i.e. the Activity, EAZ as % of catalyst bed, is estimated to be about 100 at a nitrogen to zeolite aluminum molar ratio (N/Alz) of 0.5.

While only certain embodiments have been set forth, alternatives and modifications will be apparent from the above description to those skilled in the art. These and other alternatives are considered equivalents and within the spirit and scope of this disclosure and the appended claims.

The invention claimed is:

1. An aromatic alkylation catalyst comprising a UZM-8 zeolite and nitrogen, the catalyst having a nitrogen to zeolite aluminum molar ratio of about 0.045 to about 0.5.

2. The catalyst of claim 1 further comprising a binder.

3. The catalyst of claim 2 wherein the zeolite ranges in an amount from about 5 mass percent to about 99 mass percent of the catalyst on a volatile free basis.

4. The catalyst of claim 2 wherein the zeolite ranges in an amount from about 10 mass percent to about 90 mass percent of the catalyst on a volatile free basis.

5. The catalyst of claim 2 wherein the binder comprises alumina.

6. The catalyst of claim 1 wherein an alkali and alkaline earth metal content of the catalyst is less than about 0.1 mass % on a metal oxide volatile free basis.

7. A process for producing an aromatic alkylation catalyst comprising:
   (a) forming a UZM-8 zeolite to produce a formed catalyst;
   (b) heating the formed catalyst in a first calcining step at conditions including a temperature of from about 300° C. to about 650° C. for a period of from about 10 minutes to about 20 hours to produce a calcined catalyst;
   (c) ion exchanging the calcined catalyst with an ion exchange solution comprising ammonium ions at ion exchange conditions to produce an ion exchanged catalyst;
   (d) heating the ion exchanged catalyst in a final calcining step at conditions including a temperature of from about 300° C. to about 650° C. for a period of from about 10 minutes to about 20 hours to produce the aromatic alkylation catalyst comprising the UZM-8 zeolite and nitrogen, the catalyst having a nitrogen to zeolite aluminum molar ratio of about 0.045 to about 0.5.

8. The process of claim 7 wherein the ion exchange solution is selected from the group consisting of ammonium nitrate solution, ammonium chloride solution, ammonium sulfate solution, and combinations thereof 9. The process of claim 7 wherein the ion exchange solution is an ammonium nitrate solution comprising from about 1 mass % to about 20 mass % ammonium nitrate.

10. The process of claim 7 wherein the ion exchange conditions including a temperature of about 15° C. to about 100° C. and a time of about 20 minutes to about 50 hours.

11. The process of claim 7 wherein the UZM-8 zeolite has an alkali and alkaline earth metal content greater than about 0.1 mass % on a metal oxide volatile free basis and the ion exchanged catalyst has an alkali and alkaline earth metal content less than the alkali and alkaline earth metal content of the UZM-8 zeolite.

12. The process of claim 7 further comprising drying the formed catalyst at conditions including a temperature of from about 100° C. to about 320° C. for a period of from about 1 to about 24 hours prior to the first calcining step (b).

13. The process of claim 7 further comprising drying the ion exchanged catalyst at conditions including a temperature of from about 100° C. to about 320° C. for a period of from about 1 to about 24 hours prior to the final calcining step (d).

14. An aromatic alkylation catalyst comprising a UZM-8 zeolite and nitrogen, the catalyst having a nitrogen to zeolite aluminum molar ratio of about 0.030 to about 0.5.

* * * * *